(12) United States Patent
Kawanami et al.

(10) Patent No.: US 6,274,876 B1
(45) Date of Patent: *Aug. 14, 2001

(54) INSPECTION APPARATUS AND METHOD USING PARTICLE BEAM AND THE PARTICLE-BEAM-APPLIED APPARATUS

(75) Inventors: Yoshimi Kawanami, Kokubunji; Akio Yoneyama, Musashino; Tadashi Otaka, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/657,241

(22) Filed: Sep. 7, 2000

Related U.S. Application Data

(63) Continuation of application No. 09/116,345, filed on Jul. 16, 1998, now Pat. No. 6,140,644.

(30) Foreign Application Priority Data

Jul. 18, 1997 (JP) .................................................. 9-193575

(51) Int. Cl.[7] ............................................................ G21K 5/10
(52) U.S. Cl. .................... 250/492.22; 250/307; 250/397; 250/310; 250/311; 250/396 ML; 250/396 R; 250/306
(58) Field of Search ......................... 250/492.22, 310, 250/307, 492.2

(56) References Cited

U.S. PATENT DOCUMENTS

| | | |
|---|---|---|
| 4,748,407 | 5/1988 | Brunner et al. . |
| 5,561,611 | 10/1996 | Avinash . |
| 5,825,912 | 10/1998 | Okubo et al. . |
| 5,866,905 | 2/1999 | Kakibayashi et al. . |
| 5,872,862 | 2/1999 | Okubo et al. . |
| 5,894,124 | 4/1999 | Iwabuchi et al. . |
| 5,981,947 | 11/1999 | Nakasuji et al. . |

FOREIGN PATENT DOCUMENTS

| | | |
|---|---|---|
| 60-161514 | 8/1985 | (JP) . |
| 2-181639 | 7/1990 | (JP) . |
| 5-258703 | 10/1993 | (JP) . |
| 8-273575 | 10/1996 | (JP) . |

*Primary Examiner*—Jack Berman
*Assistant Examiner*—Kalimah Fernandez
(74) *Attorney, Agent, or Firm*—Mattingly, Stanger & Malur, P.C.

(57) ABSTRACT

The inspection apparatus uses a particle beam and has a high throughput by obtaining a characteristic frequency corresponding to the characteristic quantity of focusing-shift from a Fourier spectrum of a sample image using a focusing-shift evaluator. A beam blur profile is produced corresponding to the characteristic frequency in a beam blur profile generator. A component of the beam-blur profile is removed from the sample image stored in one dimensional image memory using a de-convolution operator. A dimensional measurement is performed in a critical dimension evaluator for an obtained sample image. Since time spent for focus adjustment using particle beam scanning is obviated, it is possible to reduce the inspection time for a dimension and an appearance abnormality of a semiconductor element.

11 Claims, 11 Drawing Sheets

INSPECTION APPARATUS AND METHOD USING PARTICLE BEAM AND THE PARTICLE-BEAM-APPLIED APPARATUS

This is a continuation application of U.S. Ser. No. 09/116,345, filed Jul. 16, 1998 now U.S. Pat. No. 6,140,644.

BACKGROUND OF THE INVENTION

1. Field of the Invention

The present invention relates to a scanning microscope using a particle beam. More specifically, the present invention relates to an optimum inspection apparatus using a particle beam for performing observation or inspection of a fine dimension and/or an appearance structure of a semiconductor device.

2. Description of the Related Art

A known critical dimension evaluation apparatus using an electron beam as a particle beam acquiring a sample image based on secondary electrons by scanning an electron beam on a semiconductor sample and inspecting a dimension concerning the characteristic pattern for the sample is disclosed in Japanese Patent Application Number 60-161514. A known appearance inspection electron beam apparatus inspecting an abnormality of a sample by comparing an image of a scanning electron microscope with a standard pattern is disclosed in Japanese Patent Application Number 5-258703. A method introduced by these apparatus has high resolution for the image compared to an inspection method using an optical source and is very useful for inspecting a sub-micron semiconductor pattern.

In the prior art apparatus, an optimum focus adjustment of an electron lens system is performed based upon signals from at least 3 sample images obtained by scanning the electron beam on the same sample under different conditions of focusing shift of the electron lens system. In order to reduce the time spent for focus adjustment, a focus adjustment means for detecting a height of a sample using a height sensor using light reflection (Z sensor) and adjusting the focus of an electron lens system based upon a table produced in advance to reduce the deviation of a height of a sample from the standard is indicated in a Japanese patent application number 8-273575. Since there are such problems that a sample surface measured by the Z sensor does not completely accord with an extreme surface of the sample and that has a disadvantage in a reappearance of the focus adjustment due to hysteresis of magnetization in the electron lens system, resolution of the sample image decreased without the focus adjustment using an electron beam scanning.

A method for obtaining a high resolution for a sample image based upon mathematical conversion (integral conversion) of the sample image using a beam profile measured in advance is introduced in a Japanese patent application number 2-181639. However, this method does not consider variation of the beam profile due to variation of the focusing-shift for each spot from which the sample image is taken.

SUMMARY OF THE INVENTION

It is necessary for the above inspection apparatus to improve its throughput since a quantity for an inspection is increased by an improved resolution. However, in the prior art, time spent in adjusting a focus of the beam accompanied with the beam scanning resulting in an extreme deterioration of an inspection throughput was not taken into consideration. There is still a considerable problem that although it is necessary to execute pluralities of electron beam irradiation on a sample for performing a focus compensation, the irradiation causes contamination on the sample which varies the width of wiring circuit in the sample. Further, there is a problem that because excessive irradiation of the electron beam causes the sample to be electrified, the electron beam used to irradiate the sample is affected so that an acquired sample image causes distortion which deteriorates the accuracy of critical dimensional measurement.

An object of the present invention is to provide an inspection apparatus using a particle beam having high resolution and high throughput.

The above-mentioned object of the invention is achieved by performing a blur-separated image calculation in the inspection apparatus having a sample-image-obtaining means which scans the particle beam on a sample and a sample inspection means which uses the numerical operation of a sample image for an inspection. The inspection apparatus has a focusing-shift-detection means which derives the characteristic quantity of a focusing-shift from the sample image, a beam-blur-profile generation means which generates a beam-blur profile, corresponding to a blur of the particle beam, based upon the characteristic quantity of the focusing-shift and a blur-separation means which generates a blur-separated image based upon a separation or a reduction of a component of the beam-blur profile in the sample image.

The focusing-shift-detection means according to the present invention detects a certain spatial frequency of a Fourier spectrum of the sample image as the characteristic quantity of the focusing-shift.

Furthermore, there is provided means for memorizing by correlating the sample image, the beam-blur profile and the blur-separated image and means for displaying simultaneously a set of the sample image, the beam-blur profile and the blur-separated image.

The invention also encompasses an inspection method using the inspection apparatus. The method involves moving a sample to an inspection point for the sample after an adjustment of an astigmatism for the particle beam is completed, acquiring at most two different kinds of sample images by scanning the particle beam for each inspection point of the sample and inspecting the sample based upon the sample images.

The inspection apparatus of the present invention also includes means for producing a first display image acquired by scanning the particle beam on the sample, means for deriving the characteristic quantity of the focusing-shift based upon the first display image, means for producing a second display image based upon the characteristic quantity of the focusing-shift and the first display image and means for inspecting the sample based upon the second display image.

These and other objects, features and advantages of the present invention will become more apparent in view of the following detailed description of the preferred embodiments.

DESCRIPTION OF THE PREFERRED EMBODIMENT

Figure 1:
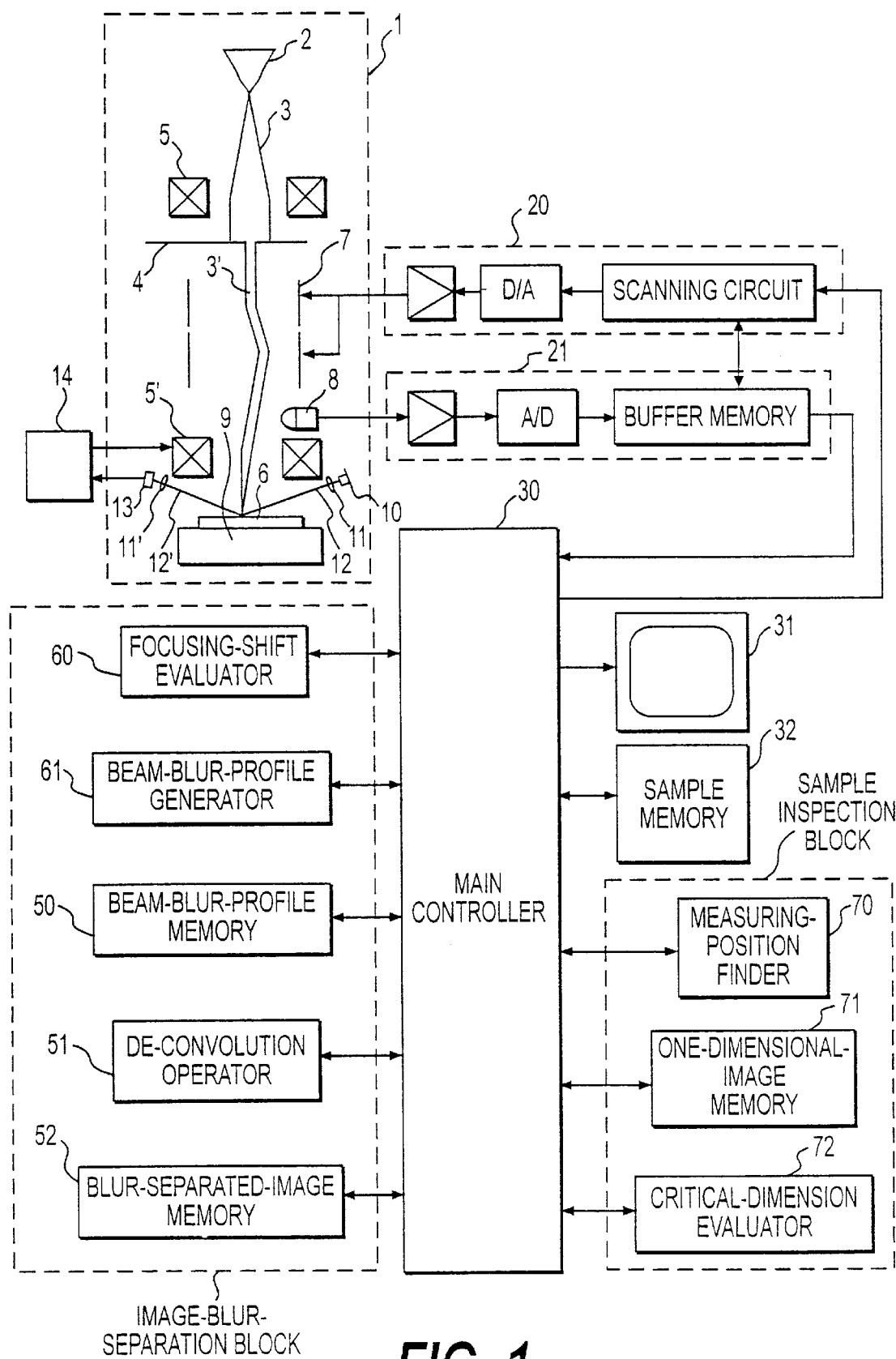
FIG. 1 is a block diagram showing an electron beam critical dimension evaluator according to an embodiment of the present invention.

In a scanning electron beam microscope, a sample image i is shown by a convolution of S and b as indicated in equation (1) on the condition that a secondary particle radiation coefficient distribution is S and an intensity distribution of a particle beam at an optimum focus is b.

$$i(x, y) = S(x, y) \otimes b(x, y) \qquad (1)$$

where (x, y) represents a two dimensional coordinate system. A convolution operation is defined by an integral conversion as indicated in equation (2).

$$S(x, y) \otimes b(x, y) = \int dX dY\, S(x + X, y + Y) b(X, Y) \qquad (2)$$

$$= \int dX dY\, S(X, Y) b(X - x, Y - y)$$

An obtained sample image I is represented by a convolution of S and B as indicated in equation (3) on the condition that an intensity distribution of the particle beam is B in case that no focus adjustment is done.

$$I(x, y) = S(x, y) \otimes B(x, y) \qquad (3)$$

where a particle beam B has a blurring of a certain amount from the particle beam b.

If a beam-blur profile showing the blurring is D, B is shown by a convolution of b and D as indicated in equation (4).

$$B(x, y) = b(x, y) \otimes D(x, y) \qquad (4)$$

Since an associative law can be used in a convolution operation, equation (5) is realized based upon equations (1), (3) and (4).

$$I(x, y) = i(x, y) \otimes D(x, y) \qquad (5)$$

If the beam-blur profile D is obtained, according to equation (5) the sample image i can be obtained at an optimum focus having a blurring removed by a reverse operation of convolution (i.e., a de-convolution operation). It should be understood that a much higher resolution of an image can be obtained if an amount close to B instead of D is used.

If a table showing a relation between a frequency spectrum appearance of sample images having several kinds of focusing-shifts and the beam-blur profile D is obtained in advance, a beam-blur profile regarding an arbitrary sample image can be produced. Further, the beam-blur profile D can be calculated by obtaining in advance several kinds of images having a focusing-shift regarding a standard sample and by comparing those images with an image at an optimum focus (perform a de-convolution operation using equation (5)).

Accordingly, the present invention obviates a focus adjustment time based upon a particle beam scanning and reduces an inspection time since a focusing-shift for the sample image of a particle beam scanning microscope based upon the introduced means can be removed. Moreover, a time for processing these operations can be reduced to a time for acquiring the sample image by using a parallel processed computer.

FIG. 1 is a block diagram showing an electron beam critical dimension evaluator based upon a first embodiment of the present invention. A main body 1 includes a FE electron source 2, a variable limiting aperture 4, electron lenses 5, 5', a deflection plate 7, a sample stage 9 movably holding a sample 6 and a secondary particle detector 8. The main body 1 also includes a laser 10, lens system 11, 11' and a laser position detector 13 for detecting a height of the sample 6. A vacuum chamber holding the above-mentioned devices and a pumping system are omitted. The secondary particle detector 8 has a fluorescence plate and a photo-multiplier, and detects secondary electrons. The main body 1 is connected to a main controller 30 via a deflection controller 20 and a secondary particle signal control system 21. A control system for the electron source 2, the variable aperture 4, the electron lens 5, and sample stage 7 is omitted. The laser position detector 13 and the electron lens 5' are connected to a focusing-lens controller 14. A display 31, a sample memory 32, a sample inspection block including a measuring position finder 70, one dimensional image memory 71 and a critical dimension evaluator 72 are connected to the main controller 30.

An operation of the main body 1 will now be described. The beam size of an electron beam 3 emitted from the electron source 2 is regulated at the variable limiting aperture 4, focused at the electron lenses 5, 5' and irradiated on the sample 6. The electron beam 3' is decelerated at the electron lens 5'. An acceleration voltage of the electron beam 3' on the sample is 800V. A beam diameter of the electron beam 3' is 5 nm and its current is 10 nA. If the electron beam 3' is irradiated on the sample 6, secondary electrons or reflection electrons corresponding to material and structure of the sample are generated from the part being irradiated. The secondary particle detector 8 detects the secondary electrons and converts to detected result into an electrical signal (a secondary electron signal). The deflectors 7 deflect the electron beam 3' and cause it to scan on the sample 6 based upon a scanning deflection signal generated from the scanning circuit in the deflection controller 20. The main controller 30 stores the secondary electron signal, with the scanning deflection signal used for addressing in a buffer memory in a secondary particle detector 21, into the sample memory 32. Simultaneously, the main controller 30 sends the secondary electron signal to the display 31 to display a SEM image (a scanning electron microscope image) of the sample having the secondary electron signal as a luminance signal. The main controller 30 still sends the sample image to the sample inspection block and performs dimensional measurement selectively at a spot being set in advance. In the sample inspection block, the measuring position finder 70 having a pattern of measuring spot in advance checks the sample image stored in the sample memory 32, instructs the main controller 30 where a required spot to measure is, has the main controller 30 derive an enlarged sample image again, generates a one dimensional image required to measure from latter image and has it stored into the one dimensional image memory 71. The critical dimension evaluator 72 abstracts a characteristic position from the one dimensional image stored in the one dimensional image memory 71 and calculates its dimension. The main controller 30 stores these calculation results into a memory device (not shown) and displays the results onto the display 31, if required. The variation of a height of the sample 6 is detected based upon the change of the position at which a reflection light 12' of a light 12 emitted from the laser 10 is incident to the laser position detector 13. The focusing lens controller 14 regulates an intensity of the electron lens 5' based upon a signal from the laser position detector 13 and always controls the electron beam 3' to focus on the sample 6. However, this method includes an inconsistent error because an optically detectable sample surface and one that is detectable by an electron beam do not match completely. Accordingly, an optimum intensity of the electron lens 5' is derived by scanning an electron beam, by obtaining several pieces of sample images having a different intensity of the electron lens 5' and by comparing those sample images with each other.

A feature of this embodiment is to (1) detect the characteristic quantity of focusing-shift from the sample image, (2) produce the beam-blur profile corresponding to the focusing-shift and (3) remove an influence of the beam-blur profile from the sample image. Specifically, as shown in FIG. 1, a feature is to have an image-blur-separation block connected to the main controller 30. The focusing-shift evaluator 60 reads the sample image obtained by scanning the electron beam 3' on the sample 6 from the sample memory 32, detects the characteristic quantity of focusing-shift based upon the appearance of Fourier spectrum for this image and sends the characteristic quantity of focusing-shift to a beam-blur-profile generator 61. The beam-blur-profile generator 61 generates a beam-blur profile from a data table held in advance for the beam blur profile corresponding to the characteristic quantity of focusing-shift through data interpolation and stores the beam-blur profile in a beam-blur-profile memory 50. A de-convolution operator 51 generates a one dimensional image of the sample at an optimum focus by performing a de-convolution operation separating a component of the beam-blur profile from the one dimensional image and stores the one dimensional image in a blur-separated image memory 52. In the prior art, the one dimensional image cut out from the sample image stored in the sample memory 32 is used in the sample inspection block for measuring a fine dimension on the sample. However, in the embodiment of the present invention, a measurement of the fine dimension is performed by removing the influence of focusing-shift and by using the one dimensional image stored in the blur-separated image memory 52. By performing this fine dimensional measurement, it is unnecessary to scan the electron beam excessively on the sample to search for the optimum focus.

Figure 2:
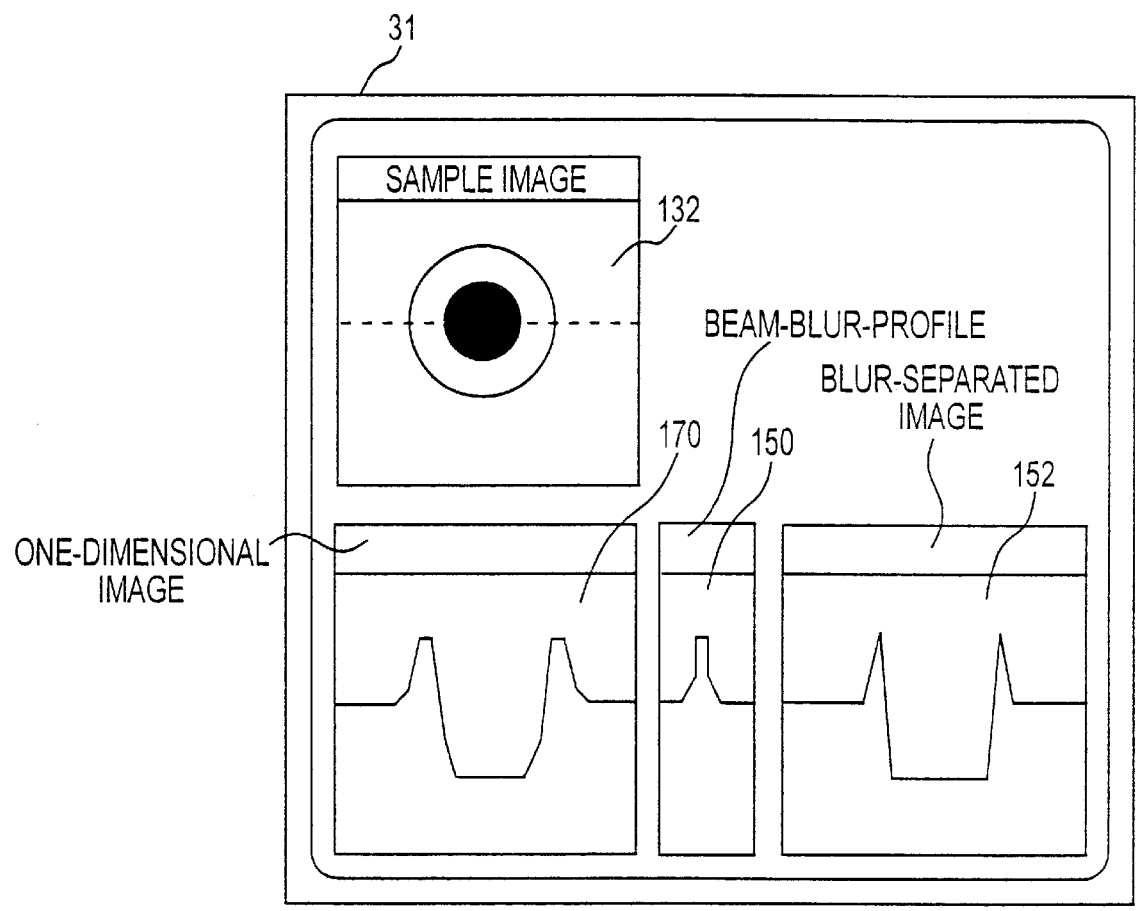
FIG. 2 is an example display.

FIG. 2 is a diagram showing an example display in which a flow for a series of the above de-convolution operations is clearly understood. A beam-blur profile 150 is generated from a sample image 132 having a slight focusing-shift. A blur-separated image 152 is generated by removing a component of the beam-blur profile 150 from the one dimensional image 170 cut out from the sample image 132 using the de-convolution operation. Then, a fine dimension (that is, a diameter of a hole) of the sample is measured by using a characteristic position of the blur-separated image 152. For the purpose of an operator's confirmation, data as shown in FIG. 2 can be put together and stored into a memory unit (not shown).

Figure 10:
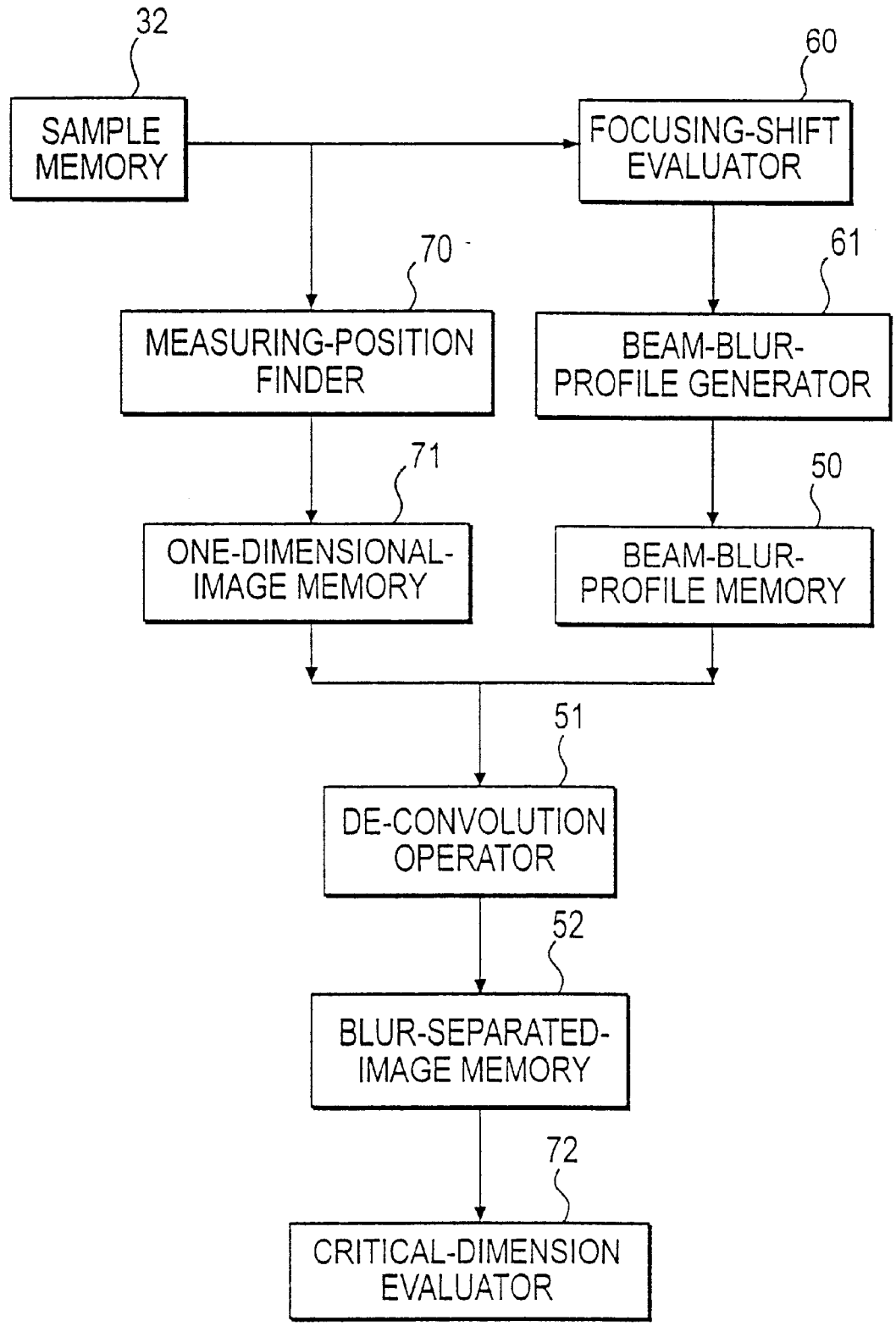
FIG. 10 is a block diagram showing a signal flow in the electron beam critical dimension evaluator according to one embodiment of the present invention.
Figure 11:
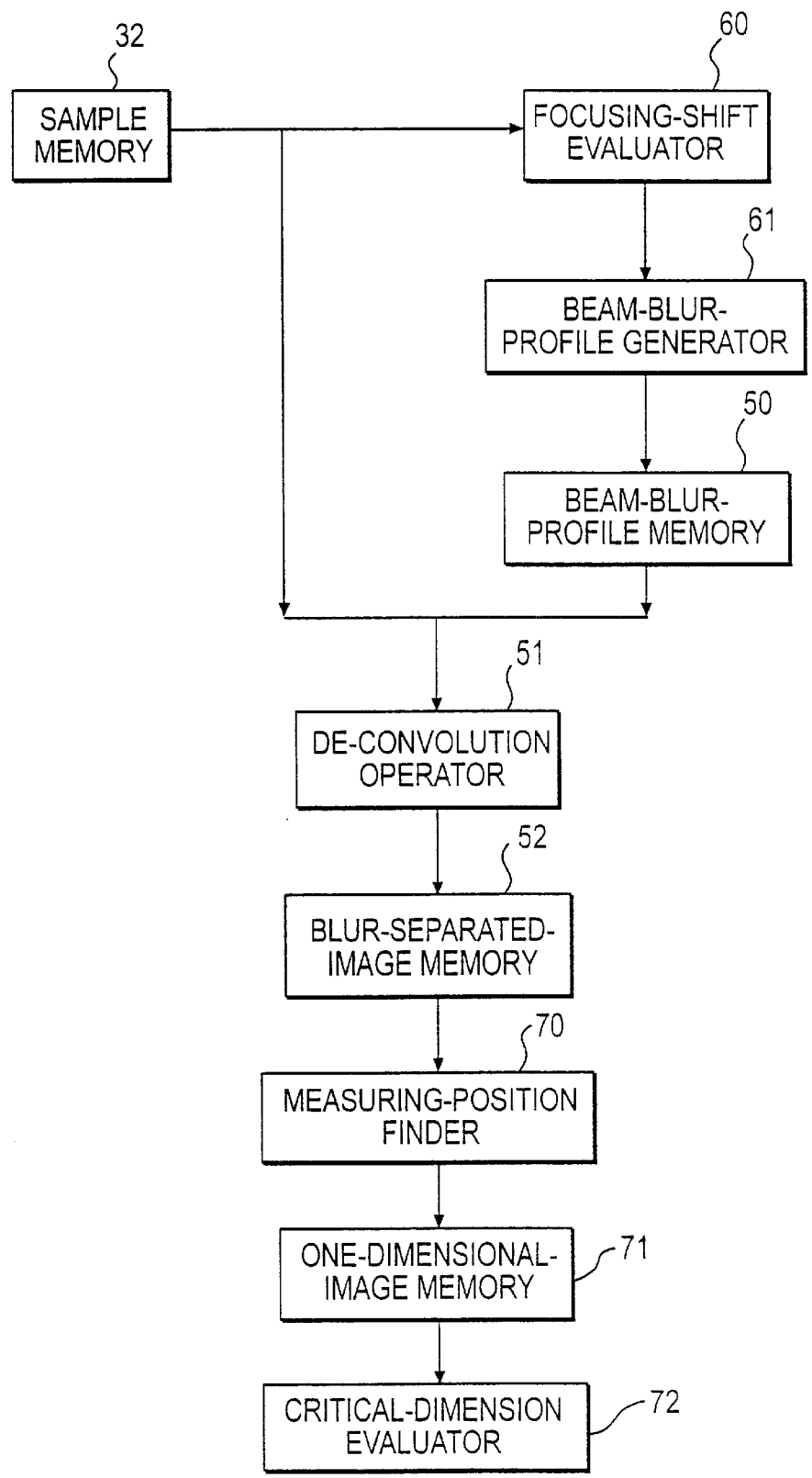
FIG. 11 is a block diagram showing another signal flow in the electron beam critical dimension evaluator according to another embodiment of the present invention.

FIG. 10 is a block diagram showing a signal flow in a process as in FIG. 2. A de-convolution operation is processed for a one dimensional image abstracted from the sample image to reduce calculation time. A method shown in FIG. 11 is appropriate to perform more accurate processing although the calculation time increases. In other words, the de-convolution operation is performed for the sample image having a two dimensional image, a measurement position is abstracted for the sample image, a one dimensional image is produced and a critical dimension evaluation is performed.

Figure 3:
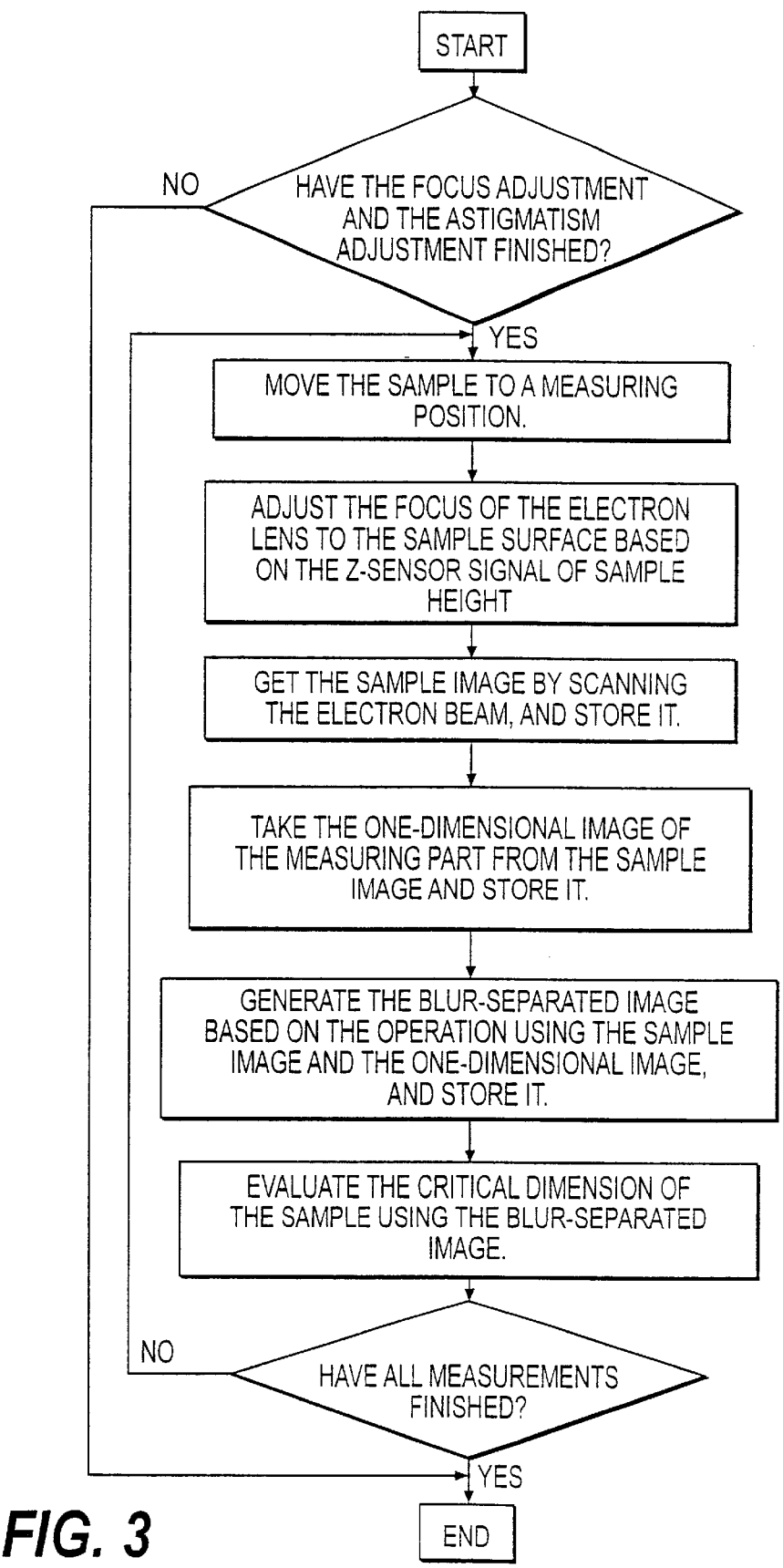
FIG. 3 is a flow chart of a dimension measurement process.

FIG. 3 is a flow chart showing the steps of measurement. A feature of FIG. 3 is to perform a focus adjustment and an adjustment of the astigmatism for an electron beam using a standard sample being set on the sample stage. Another feature is that dimensional measurement can not be performed unless this adjustment is completed. The latter feature is a remedy to deterioration of accuracy for the blur-separated image produced by the de-convolution operation since the beam-blur profile is not produced normally if the adjustment of the astigmatism is not performed. An electron beam critical dimension evaluator introduced in an embodiment of the present invention is programmed to end abnormally and to display an abnormality to an operator in case that the above focus adjustment and the adjustment of the astigmatism result in failure during a normal automatic measurement. If the adjustment is completed normally, the sample is moved to put an arbitrary position of the sample registered in advance just below the electron beam. Detection of a height of the sample using the Z sensor and focus adjustment of the electron lens are performed simultaneously with this sample movement. Then a sample image is derived by scanning the electron beam on the sample, the image is stored, a one dimensional image required for dimensional measurement is cut out and the one dimensional image is stored thereafter. For deriving the sample image, deriving an enlarged sample image again for adjusting to a necessary scale factor often occurs. Accordingly, in a procedure for the following dimensional measurement, the number of sample images obtained by the electron beam scanning is one or two (ie. at most two). Then a blur-separated image is produced from a stored sample image and one dimensional image, and a dimensional measurement for this blur-separated image is performed. If the above procedure is ended, the same procedure is repeated after moving to the next sample position. Further, in FIG. 3, although an acquisition of the sample image and a measurement of dimension are performed simultaneously, it is possible to perform them separately.

In the prior art, it took 10 seconds to complete a critical dimension evaluation at a spot of a sample. The contents of the evaluation includes: 2 seconds for a focus adjustment by moving the sample and using the Z sensor; 5 seconds for the focus adjustment by scanning a beam; 2 seconds for deriving a sample image and detecting a characteristic position; and 1 second for producing and inspecting the one dimensional image. In the embodiment of the present invention, it takes 6 seconds to finish measurement as a whole so that a second for producing a blur-separated image is added while the focus adjustment by a beam scanning is unnecessary. It is possible for the blur-separated image to reduce its production time according to a parallel computerization.

Figure 4:
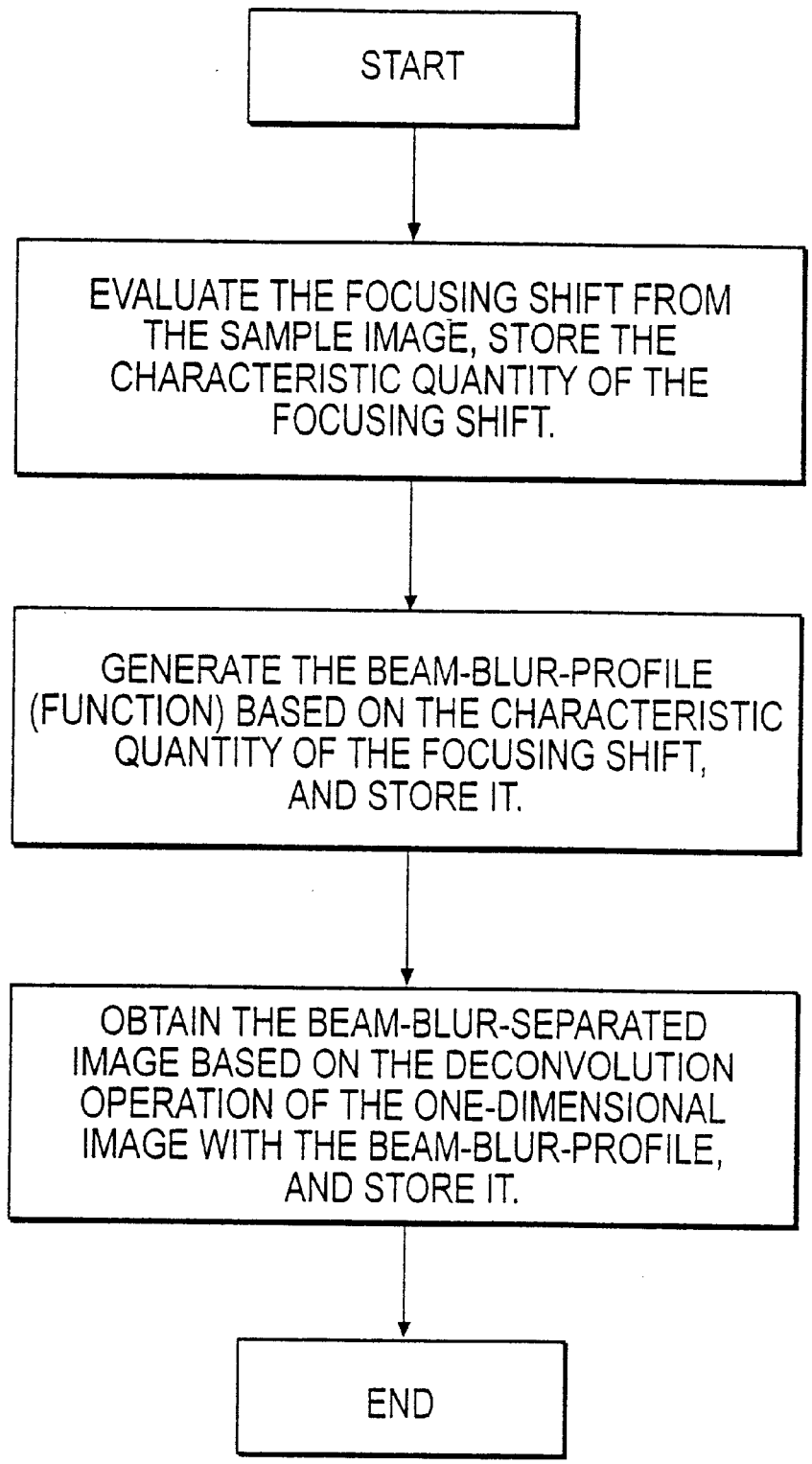
FIG. 4 is a flow chart for generating a blur-separated image.
Figure 5:
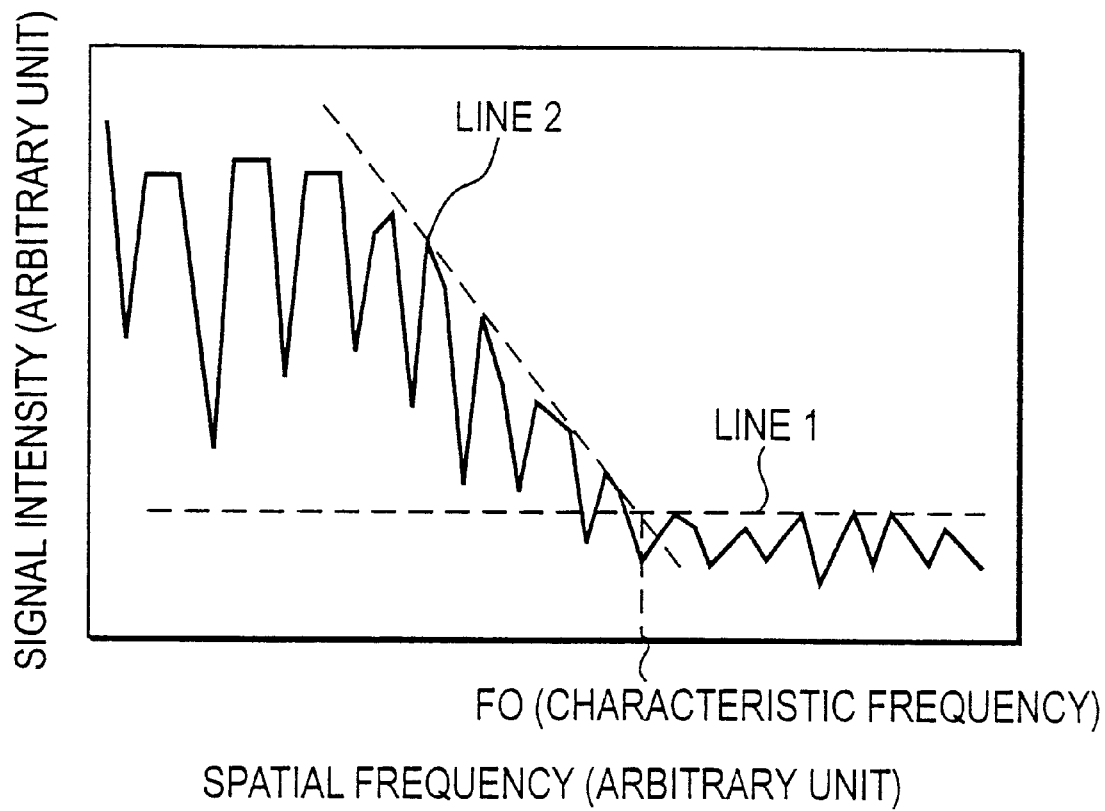
FIG. 5 is a graph showing an example Fourier spectrum of a sample image.

FIG. 4 is a flow chart showing the generation of a blur-separated image as in FIG. 3. A detailed description is given for detecting the characteristic quantity of focusing-shift, i.e., the content of focusing-shift evaluator 60 as in FIG. 1. The sample images read from the sample memory are all integrated in one dimensional direction. Then Fourier transform is applied to a signal resulting from the integration. In this case, an intensity of the Fourier transformed result is standardized as a total signal amount. An image applied Fourier transform (that is, a Fourier spectrum) is shown in FIG. 5. An optimal intensity close to a noise level is set. LINE 1 in FIG. 5 shows the optimal intensity. An asymptotic line for a variation part of the Fourier spectrum is shown as LINE 2. A spatial frequency F0 calculated based upon an intersection of LINE 1 and LINE 2 is detected as the characteristic quantity of focusing-shift. Although a focusing-shift evaluation is performed for the sample image, the same evaluation may be done for the one dimensional image. In such case, since S/N (signal to noise ratio) of a signal gets worse slightly, the accuracy of calculation also decreases. However, calculation time can be reduced.

Figure 6A:
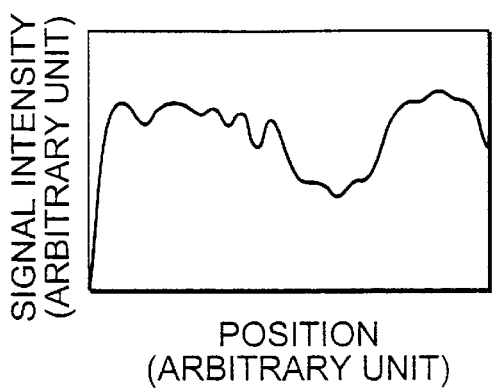
FIGS. 6(a)–6(f) are graphs showing a sample image in several kinds of focusing-shifts and their corresponding Fourier spectrum.
Figure 6B:
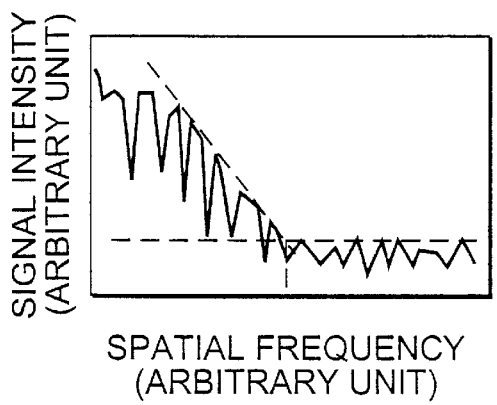
Figure 6C:
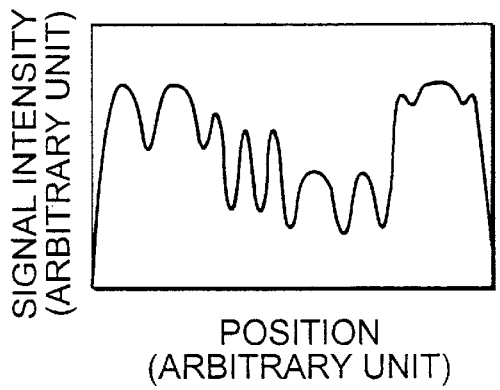
Figure 6D:
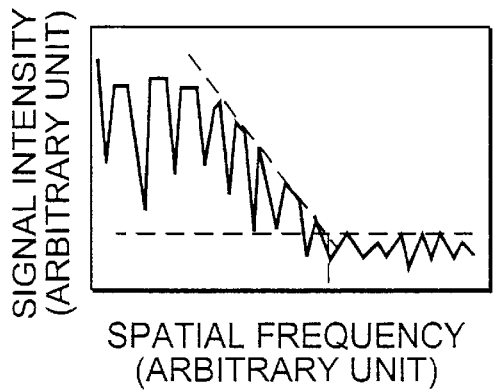
Figure 6E:
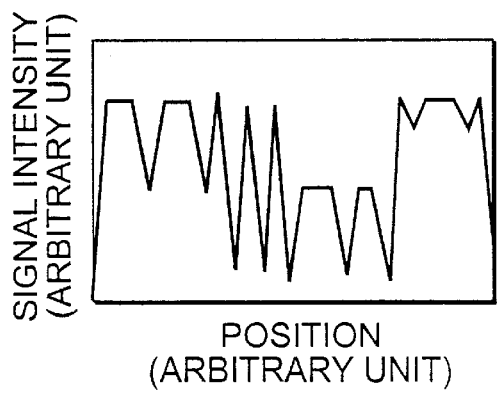
Figure 6F:
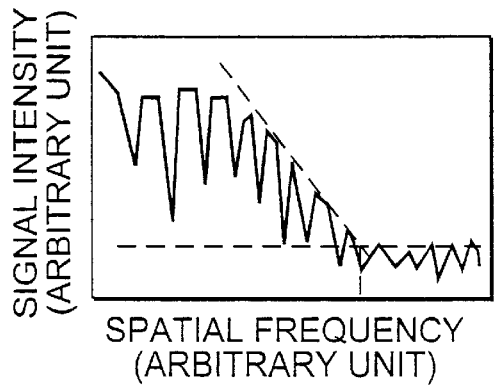

FIGS. 6(a)–6(f) are graphs showing a sample image in case of setting several kinds of focusing-shifts regarding a standard sample intentionally and an example of a Fourier spectrum. FIGS. 6(a) and 6(b) correspond to a sample image with a great shift of focusing. FIGS. 6(c) and 6(d) correspond to a sample image with a small shift of focusing. FIGS. 6(e) and 6(f) correspond to a sample image with optimum focus. The sample image is already integrated one-dimensionally and an intensity is standardized. The characteristic quantity of focusing-shift as in FIGS. 6(a)–6(f) is on a level that a Z sensor can not compensate and is a very small amount. Since a spatial frequency F0 varies with respect to the focusing-shift, it is understandable to convert the frequency F0 to the characteristic quantity of focusing-shift and to read it. Further, it is possible to obtain a beam-blur profile based upon a de-convolution operation of the sample image at the optimal focus from the sample image at an arbitrary focus and to generate a table showing the relationship between the spatial frequency F0 and the beam-blur profile (it is necessary to increase S/N of the sample image and to widen a dynamic range for obtaining the beam-blur profile as accurately as possible). The beam-blur profile generator 61 in FIG. 1 holds this table and produces a beam-blur profile based upon a compensation of the data table for an arbitrary spatial frequency. Here, a height of LINE 1 and a slope of LINE 2 are respectively, determined by the characteristics of beam-blur function, common for an electron beam critical dimension evaluator of the same electron optical system design (that is product-type). However, they are slightly varied for each apparatus of the same product-type. Because of this feature, in the electron beam critical dimension evaluator introducing an embodiment of the present invention, data held in the focusing-shift evaluator 60 and the beam-blur-profile generator 61 is divided into a common specification portion and a compensation portion and a data of the compensation portion is restored for each apparatus. A standard sample is set on a sample stage for performing such correction operation. A program performing correction operation automatically using this standard sample is installed in the main controller 30. Although a focusing-shift beam blur profile is produced based upon the table, it is possible to produce the beam blur profile using an appropriate approximation function. When using such approximation function, computing time can be reduced.

Figure 7:
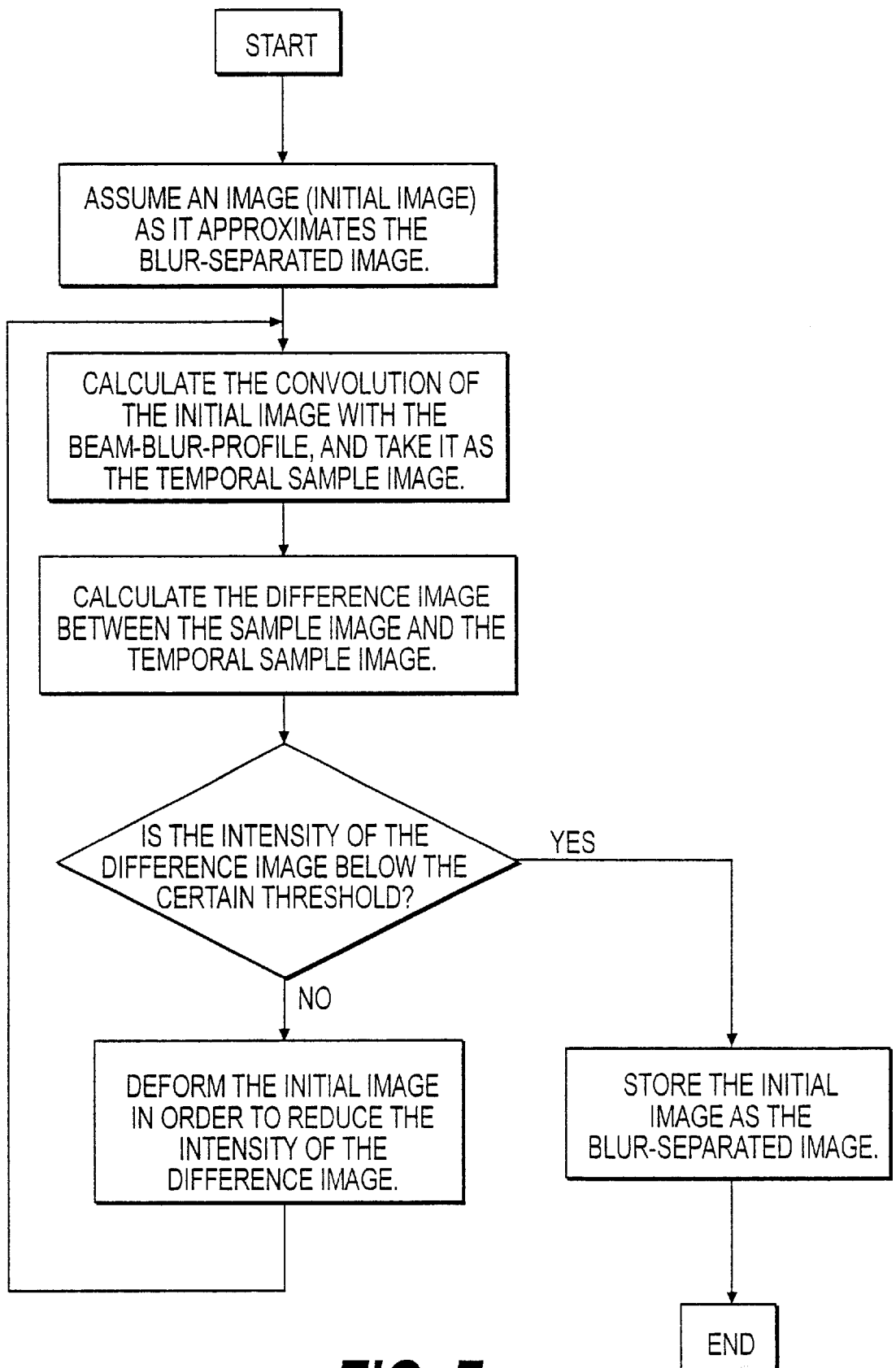
FIG. 7 is a flow chart of a de-convolution operation.

A description concerning a de-convolution operation performed in the de-convolution operator 51 in FIG. 1 will now be described. In the embodiment of the present invention, a feature is that a method using a convolution operation and a repetitive comparison is employed instead of a simple de-convolution operation. Such a method has a tolerance to noise. FIG. 7 is a flow chart showing a de-convolution operation. An operation of this flow chart includes: (1) assuming an appropriate blur-separated image (first blur-separated image) initially; (2) obtaining a result for a convolution operation of the first blur-separated image and a beam-blur profile; (3) obtaining a difference image for them by comparing the result with an actual sample image; and (4) compensating the first blur-separated image to decrease an intensity of the difference image and returning to a step (2). The above operation is a repetitive process. Further, the above operation converges through repetitive process of more than 10 times and the operation time is approximately 100 ms using a special purpose circuit having sum-of-products operation paralleled.

Since a focus adjustment based upon an electron beam scanning can be obviated by employing the embodiment of the present invention, there is an effectiveness to be able to reduce damage for a sample such as a semiconductor element due to electron beam irradiation and dimensional measurement time can be reduced.

Figure 8:
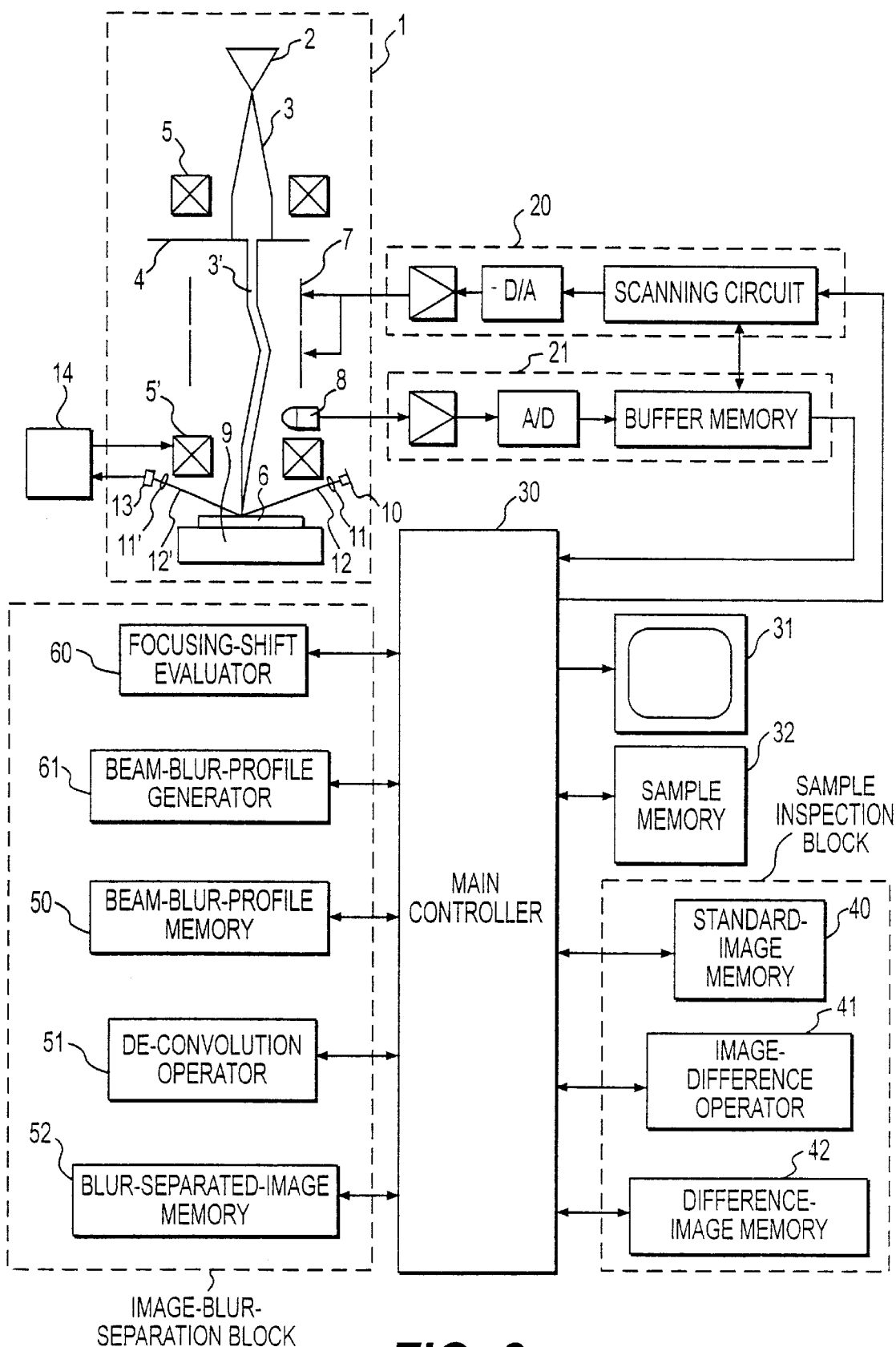
FIG. 8 is a block diagram showing an appearance inspection electron beam apparatus according to an embodiment of the present invention.

FIG. 8 is a block diagram showing an appearance inspection electron beam apparatus based upon a second embodiment of the present invention. A configuration as a whole is as well as the electron beam critical dimension evaluator shown in FIG. 1. An internal configuration of a sample inspection block connected with a main controller 30 and a configuration of a program built in the main controller 30 are different from those in FIG. 1. Although detailed design of an electron optical system and a secondary particle detector are different as well, a description of the difference is omitted since the difference is less important. A beam diameter of an electron beam 3' is 100 nm and its current is 100 nA. The sample inspection block includes a standard-image memory 40, an image-difference operator 41 and a difference-image memory 42. The main controller 30 reads a sample image obtained by scanning the electron beam 3' on a sample 6 from a sample memory 32, sends the sample image to the sample inspection block and detects a sample abnormality such as foreign matters by comparing the sample image with a standard image. In the sample inspection block, the sample image stored in the sample memory 32 and a standard display image stored in advance in the standard image memory 40 are compared by the image-difference operator 41 and the comparison result is stored in the difference-image memory 42. If the difference image satisfies an arbitrary standard, the image is stored as an abnormality in a memory unit (not shown) and is displayed in the display 31.

A feature of this embodiment is to (1) detect the characteristic quantity of focusing-shift from the sample image, (2) produce a beam-blur profile corresponding to the focusing-shift and (3) remove an influence of the beam-blur profile from the sample image. Specifically, as shown in FIG. 8, a feature is to have an image-blur-separation block connected to the main controller 30. A focusing-shift evaluator 60 reads a sample image from the sample memory 32, detects the characteristic quantity of focusing-shift based upon an appearance of a Fourier spectrum of this sample image and sends the characteristic quantity to a beam-blur-profile generator 61. The beam-blur-profile generator 61 generates a beam-blur profile from the data table held in advance for the beam blur profile corresponding to the characteristic quantity of focusing-shift through data interpolation and stores the beam-blur profile into a beam-blur-profile memory 50. A de-convolution operator 51 generates a sample image at an optimum focus by performing a de-convolution operation separating a component of the beam-blur profile from the sample image and stores the sample image to a blur-separated image memory 52. An appearance inspection of the sample is performed by comparing the sample image stored in the blur-separated image memory 52, having an influence of the focusing-shift removed, with a standard image stored in the standard image memory 40. Based upon this inspection, it is unnecessary to scan an electron beam on the sample excessively and the inspection can be performed by using the sample image at an optimum focus.

Figure 9:
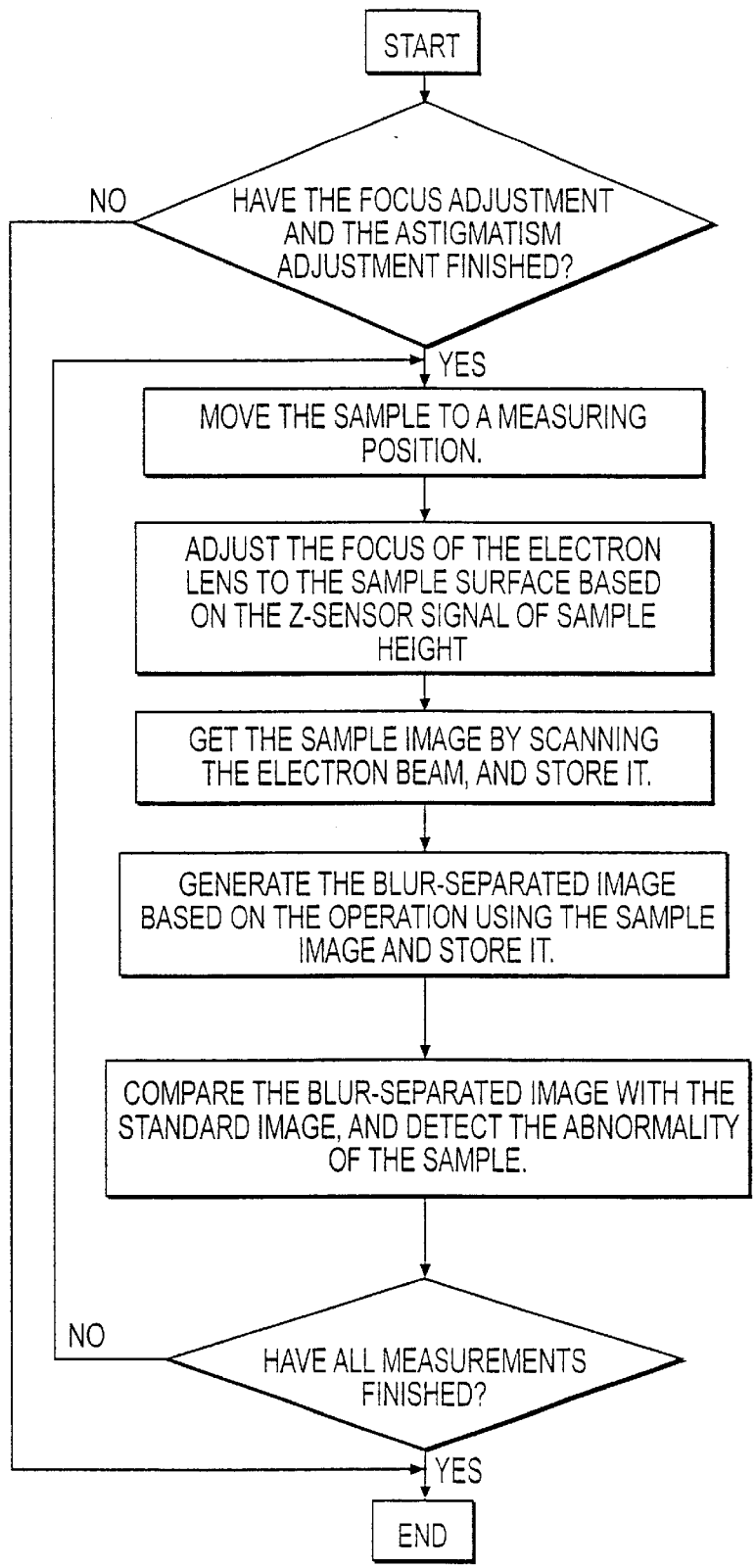
FIG. 9 is a flow chart of an appearance inspection.

FIG. 9 is a flow chart showing a performance of an appearance inspection. Just as with the embodiment shown in FIG. 1, an appearance inspection electron beam apparatus is set not to be able to perform an appearance inspection unless a focus adjustment and an adjustment of the astigmatism is completed. If the above adjustment is normally done, the sample is moved to put an arbitrary position of the sample registered in advance just below the electron beam. Detection of a height of the sample using a Z sensor and a focus adjustment of an electron lens are performed simultaneous with this sample movement. Then the sample image is derived by scanning the electron beam on the sample and the image is stored. A blur-separated image is produced from the stored sample image. An appearance inspection of the sample is performed for this blur-separated image and foreign matters on the sample are detected. If a series of steps according to the above procedure is ended, the same procedure is repeated after moving to the next sample position. Further, in FIG. 9, although an acquisition of the sample image and its appearance inspection are performed simultaneously, it is possible to perform them separately.

In the prior art, it took 100 ms to perform an appearance inspection for a spot of the sample. This time is almost equal to an acquisition time of a sample image since the sample image is derived while moving a sample stage. Although a resolution of the sample image at an optimum focus obtained by scanning an electron beam several times on the sample is 100 nm, an average resolution of the sample image in case of a focus adjustment using a Z sensor is 200 nm. In the embodiment of the present invention, since a sample image at an effectively optimum focus is derived and an appearance inspection for that focus is performed, resolution of the inspection is improved many times as much. The time spent for an operation in the image blur-separation block as in FIG. 9 is 100 ms using a special purpose circuit having sum-of-products operation paralleled. However, since the special purpose circuit portion is arranged by two channels being paralleled and multiplied, an influence to an actual inspection time is completely removed.

Through embodiments of the present invention, an appearance inspection using a sample image at an effectively optimum focus is performed, thereby improving resolution of an inspection.

According to the present invention, since the time spent for focus adjustment based upon the particle beam scanning is obviated, it is possible to reduce an inspection time for a dimension and an appearance abnormality of a semiconductor element. Further, there is provided an improved accuracy of the inspection since contamination and/or electrification of the sample based upon an excessive irradiation of the electron beam can be reduced. Additionally, a defection analysis of a semiconductor integrated circuit is performed during a short period of time. Hence, there is another advantage to improve its yield rate in an early stage.

While the present invention has been described above in conjunction with the preferred embodiments, one of ordinary skill in the art would be enabled by this disclosure to make various modifications to these embodiments and still be within the scope and spirit of the present invention as defined in the appended claims.

What is claimed is:

1. A method of measuring a fine dimension of an object sample comprising the steps of:

generating a charged particle beam;

irradiating said charged particle beam to an object sample;

detecting secondary charged particles radiated from said object sample;

generating a plurality of first values of characteristic quantity of focusing shift from a plurality of Fourier spectrum of charged particle-beam profiles of a standard sample respectively obtained at different focus shift quantities and a second value of characteristic quantity of focusing shift from a Fourier spectrum of a charged particle-beam profile of said object sample;

storing said charged particle-beam profiles of standard sample respectively corresponding to said first values of characteristic quantity, and said first values of characteristic quantity of focus shift of said standard sample and a second value of characteristic quantity of focus shift of said object sample;

estimating a beam-blur profile of said standard sample which corresponds to said second value of characteristic quantity from charged particle-beam profiles stored in said memory; and generating a blur-separated image based upon a reduction of said charged particle-beam from said object sample image using a de-convolution operations.

2. The method according to claim 1, wherein said charged particle beam generated in said step of generating a charged particle-beam is an electron beam.

3. An inspection apparatus employing a particle-beam having a sample-image-obtaining means for scanning said particle-beam on an object sample, the apparatus comprising:

a focusing-shift-evaluator which generates a plurality of first values of characteristic quantity of focusing shift from a plurality of Fourier spectrum of particle-beam profiles of a standard sample respectively obtained at different focus shift quantities, and a second value of characteristic quantity of focusing shift from a Fourier spectrum of a particle-beam profile of said object sample;

a memory for storing said particle-beam profiles of said standard sample respectively corresponding to said first values of characteristic quantity and said first values of characteristic quantities of focus shift of said standard sample and said second value of characteristic quantity of focus shift of said object sample;

a beam-blur-profile generator which estimates a beam-blur profile of said standard sample which corresponds to said second value of characteristic quantity from particle-beam profiles stored in said memory; and blur-separation means which generates a blur-separated image based upon a reduction of said particle-beam from said object sample image using a de-convolution operation.

4. The inspection apparatus according to claim 3, wherein said first values of characteristic quantity are respective spatial frequencies required from each Fourier-spectrum of said particle-beam profiles.

5. The inspection apparatus according to claim 3, further comprising:

a display unit for displaying a set of said object sample image, said particle-beam profile of said object sample and said blur-separated image of said object sample.

6. An inspection method using a particle beam comprising the steps of:

performing an adjustment of an astigmatism for said particle beam;

moving an object sample to one of a plurality of inspection points set in advance for said object sample;

evaluating a plurality of first values of characteristic quantity of focusing shift from a plurality of Fourier spectrum of particle-beam profiles of a standard sample respectively obtained at different focus shift quantities and a second value of characteristic quantity of focusing shift from a Fourier spectrum of a particle-beam profile of said object sample;

storing said particle-beam profiles of said standard sample respectively corresponding to said second value of characteristic quantity, and said first values of characteristic quantity of focus shift of standard sample and second value of characteristic quantity of focus shift of said object sample;

estimating beam-blur profiles of said standard sample which correspond to said second value of characteristic quantity from said particle-beam profiles stored in said first memory; and separating a blur-separated image based upon a reduction of said second focus shift of said object sample using a de-convolution operation.

7. The method according to claim 6, wherein the step of moving the object sample includes a step of detecting a height of the object sample using a Z sensor while the object sample is being moved.

8. The method according to claim 7, wherein the step of moving the object sample also includes a step of performing focus adjustment of the electron lens while the object sample is being moved.

9. The method according to claim 6, wherein the beam blur profiles estimated in said step of estimating said beam blur profiles are one dimensional images.

10. The method according to claim 6, wherein the step of estimating beam blur profiles corresponding to said second value of characteristic quantity estimates by interpolating from said plurality of particle beam profiles of said standard sample.

11. The method according to claim 8, wherein the step of inspecting said object sample includes the steps of:

producing a blur-separated image from a stored sample image and a one dimensional image; and performing a dimensional measurement for the blur-separated image.

* * * * *